United States Patent
Allen et al.

(10) Patent No.: US 9,433,551 B2
(45) Date of Patent: Sep. 6, 2016

(54) PROTECTION DEVICE FOR SURGERY TABLES

(71) Applicants: Robert Dan Allen, Newbury, OH (US); Jimmie Vincent Leanza, Windsor, OH (US)

(72) Inventors: Robert Dan Allen, Newbury, OH (US); Jimmie Vincent Leanza, Windsor, OH (US)

(*) Notice: Subject to any disclaimer, the term of this patent is extended or adjusted under 35 U.S.C. 154(b) by 0 days.

(21) Appl. No.: 14/658,723

(22) Filed: Mar. 16, 2015

(65) Prior Publication Data

US 2015/0257958 A1    Sep. 17, 2015

Related U.S. Application Data (60) Provisional application No. 61/953,043, filed on Mar. 14, 2014.

(51) Int. Cl.
| | | |
|---|---|---|
| *A47C 31/00* | (2006.01) | |
| *A61G 13/10* | (2006.01) | |
| *A61G 13/04* | (2006.01) | |
| *A61G 13/06* | (2006.01) | |
| *A61G 13/08* | (2006.01) | |

(52) U.S. Cl.
CPC .............. *A61G 13/10* (2013.01); *A61G 13/101* (2013.01); *A61G 13/04* (2013.01); *A61G 13/06* (2013.01); *A61G 13/08* (2013.01)

(58) Field of Classification Search
CPC ............... A61G 13/12; A61G 13/101; A61G 13/1235; A61G 13/1245; A61G 13/10; A61G 13/08; A61B 19/28
USPC ............ 248/447, 201, 291.1, 124.1; 108/49; 5/507.1, 317 R, 600, 658; 128/200.24
See application file for complete search history.

(56) References Cited

U.S. PATENT DOCUMENTS

| | | | | |
|---|---|---|---|---|
| 2,628,803 | A * | 2/1953 | Krewson | A61M 16/06 128/200.24 |
| 3,859,993 | A * | 1/1975 | Bitner | A61G 10/04 128/200.24 |
| 4,113,218 | A * | 9/1978 | Linder | A61G 13/10 248/124.1 |
| 4,381,572 | A * | 5/1983 | Thumberger | A47C 20/022 5/651 |
| 4,730,725 | A | 3/1988 | Marshall, Sr. et al. | |
| 5,152,486 | A * | 10/1992 | Kabanek | A61G 13/10 108/49 |
| 5,362,021 | A * | 11/1994 | Phillips | A61G 13/101 248/124.1 |
| 5,871,015 | A | 2/1999 | Lofgren et al. | |
| 6,446,285 | B1 * | 9/2002 | Chinn | A61G 1/04 108/49 |
| 7,980,517 | B2 | 7/2011 | Zoland et al. | |

* cited by examiner

*Primary Examiner* — Anita M King
(74) *Attorney, Agent, or Firm* — Pearne & Gordon LLP (57) ABSTRACT

A patient protection device is provided for an operating room table. A rigid support frame extends transversely over a top surface of said table, including a main body with an upper support surface and a pair of support legs that are secured to the table. A receptacle tray to receive medical equipment is securely mounted to the rigid support frame via a removable connection. The receptacle tray includes a first planar surface positioned above a body lying over said top surface of said operating room table. The receptacle tray is slidable, relative to the rigid support frame, along a direction substantially parallel to the upper support surface of the rigid support frame.

20 Claims, 6 Drawing Sheets

PROTECTION DEVICE FOR SURGERY TABLES

CROSS-REFERENCE TO RELATED APPLICATIONS

This application claims the benefit of U.S. Provisional Application No. 61/953,043, filed Mar. 14, 2014, the entire disclosure of which is hereby incorporated herein by reference.

FIELD OF THE INVENTION

The present invention relates generally to a patient protection device for surgery tables, and more particularly, to a patient protection device for an operating room table that also provides a receptacle tray to hold surgical instruments.

BACKGROUND OF THE INVENTION

A number of operating room table accessory devices have been developed in an attempt to protect patients from harm while they are restrained upon an operating room table during a medical procedure, and especially when the table is tipped into a head down angulation. This position is known in the industry as the Trendelenburg position, and the angle of head down tilt typically ranges from 20° to 50° with respect to a ground surface. The Trendelenburg position is often utilized when internal visualization of and access to the pelvis is required for robotic assisted laparoscopic surgery, minimally invasive surgery and traditional open surgery. When the Trendelenburg position is achieved, gravity causes the internal organs to shift toward the head thereby improving visualization and surgeon access to the pelvic anatomy. With the advent of robotic assisted laparoscopic surgery, many procedures are done in the most extreme Trendelenburg postures available from the surgical table. Even so, patient safety remains of the utmost concern.

Conventionally, surgical instruments that are used during surgical procedures by surgeons are commonly laid out on a table called a "mayo stand." A mayo stand is often a movable table that includes a rectangular frame horizontally cantilevered from an upstanding leg. A fixed or movable base at the bottom of the upstanding leg to provides stability and often mobility to the mayo stand. A removable or non-removable instrument tray is supported at the upper end of the frame. A sterile material may cover the instrument tray. During a surgical procedure, the sterile mayo stand is moved close to the surgical site so that the instruments and other supplies placed on the tray may be readily available to the surgeon directly or to an assistant that hands the requested instrument to the surgeon.

This instant invention results from an attempt to provide an innovative device that eliminates or minimizes intraprocedural patient injury, provides a stable and secure surface for the temporary storage of surgical instruments, meets or exceeds the clinical guidelines in the medical literature regarding needs for safety, and provides fast and easy anesthesia access and exposure.

It is to be understood that both the foregoing general description and the following detailed description present example and explanatory embodiments of the invention, and are intended to provide an overview or framework for understanding the nature and character of the invention as it is claimed. The accompanying drawings are included to provide a further understanding of the invention and are incorporated into and constitute a part of this specification.

The drawings, photographs, and attachments illustrate various example embodiments of the invention, and together with the description, serve to explain the principles and operations of the invention.

BRIEF SUMMARY OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect of the present invention, a patient protection device is provided for an operating room table. A rigid support frame extends transversely over a top surface of said table, and comprises a main body with an upper support surface and a pair of support legs that are secured to said table to inhibit movement of the upper support surface along a longitudinal axis of said table. A receptacle tray to receive medical equipment is securely mounted to the rigid support frame via a removable connection. The receptacle tray comprises a first planar surface that is substantially parallel to a top surface of said operating room table and a second planar surface arranged at an angle relative to the first planar surface. The receptacle tray is slidable, relative to the rigid support frame, along a direction substantially parallel to the upper support surface of the rigid support frame. In an operative position, the first and second planar surfaces are positioned above a body lying over said top surface of said operating room table.

In accordance with another aspect of the present invention, a patient protection device is provided for an operating room table. A rigid support frame extends transversely over a top surface of the table and comprises a main body defining an upper support surface with a recessed channel. A pair of depending projections extend downwards from the main body, and a pair of support legs each connected to a selected one of the depending projections and secured to said table to inhibit movement of the upper support surface along a longitudinal axis of said table. Each support leg is pivotally connected to said selected one of the depending projections of the main body of the rigid support frame so that the main body of the rigid support frame can pivot relative to said top surface of said operating room table. A receptacle tray is provided to receive medical equipment and is securely mounted to the rigid support frame via a removable connection. The receptacle tray comprises a first planar surface that is substantially parallel to a top surface of said operating room table, and a channel insert that is received within and horizontally slidable along the recessed channel of the rigid support frame so that the receptacle tray is slidable, relative to the rigid support frame, along said longitudinal axis of said table. In an operative position, the first planar surface is positioned above a body lying over said top surface of said operating room table.

It is to be understood that both the foregoing general description and the following detailed description present example and explanatory embodiments of the invention, and are intended to provide an overview or framework for understanding the nature and character of the invention as it is claimed. The accompanying drawings are included to provide a further understanding of the invention and are incorporated into and constitute a part of this specification.

The drawings illustrate various example embodiments of the invention, and together with the description, serve to explain the principles and operations of the invention.

BRIEF DESCRIPTION OF THE DRAWINGS

The foregoing and other aspects of the present invention will become apparent to those skilled in the art to which the present invention relates upon reading the following description with reference to the accompanying drawings, in which.

DESCRIPTION OF EXAMPLE EMBODIMENTS

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

The present application relates generally to a patient protection device 20 for surgery tables, and more particularly, to a patient protection device for an operating room table that also provides a receptacle tray to hold surgical instruments that are used during or after any surgical procedure or intervention. The various objectives of the invention are to provide a safe environment for the patient's head and face during any surgical procedure while also providing an improved instrument receptacle tray located above the patient during the surgical intervention. This instant invention results from an attempt to provide an innovative device that is capable of being utilized: (1) as a solution to protect the patient's face from injury, increase the anesthesia care giver's access to monitoring the patient's breathing and other vital signs; (2) to provide a safe surface for surgeon(s) and assistant(s) to temporarily hold surgical instruments; and (3) to provide an efficient system that can be quickly and easily modified or removed in the event of an emergency to provide quick, easy, and complete access to the patient's body.

The patient protection device 20 includes at least two major elements. The first element is a rigid support frame 22, and the second element is an instrument receptacle tray 30. The rigid support frame 22 is used for the support and attachment of the instrument receptacle tray 30 onto the surgical table.

Figure 1:
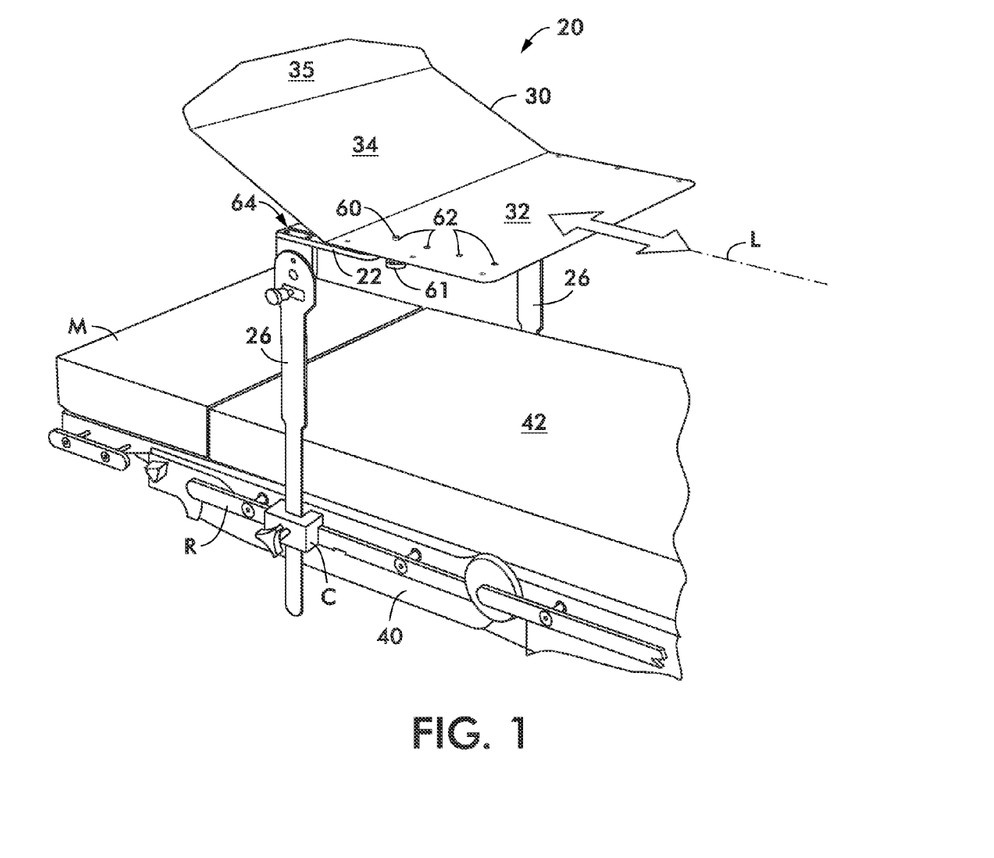
FIG. 1 illustrates a perspective view of a first example patient protection device for a surgery table.
Figure 2:
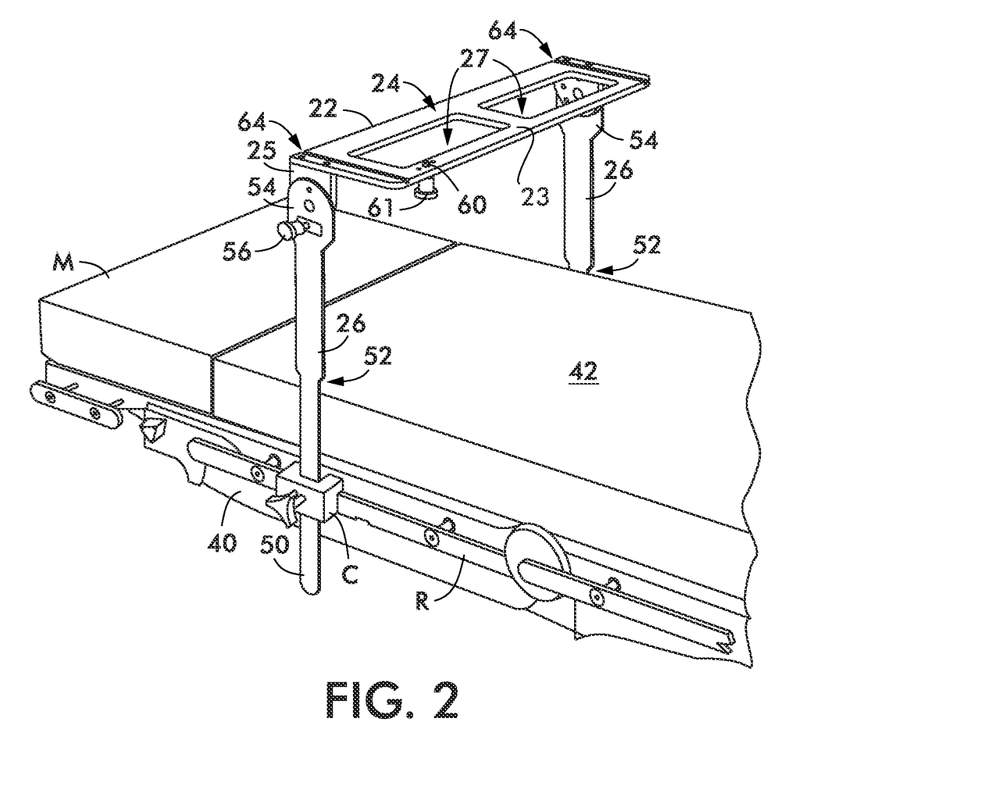
FIG. 2 illustrates an example rigid support frame of the patient protection device.

In some embodiments and in association with the operating room table, turning now to FIGS. 1-2, the rigid support frame 22 extends transversely over the top surface 42 of the operating room table 40. The top surface 42 can include a top surface of the tabletop or a top surface of a mattress M lying over the tabletop. The rigid support frame 22 includes a main body 23 that defines an upper support surface 24 and a pair of legs 26 that are secured to the operating room table 40 to inhibit movement of the rigid support frame 22 and upper support surface 24 along a longitudinal axis L of the table 40. The rigid support frame 22 can have varying widths and depths spanning across the top surface 42 of the table 40. Although only a single support frame is illustrated, it is contemplated that two or more support frames can be used. In one example, the main body 23 of the rigid support frame 22 can extend transversely over the top surface 42 of the table 40 so as to be substantially perpendicular to the longitudinal axis L of the table 40, although in other examples the rigid support frame 22 extends transversely over the top surface of the table at other angles. The rigid support frame 22 is preferably made of durable, rigid materials that are suitable for use in an operating room and surgical setting, such as various metals (e.g., stainless steel, aluminum, etc.) and plastics. Such materials may or may not be radiolucent.

The rigid support frame 22 is attached to the operating room table 40 by the pair of legs 26 at each end of the support frame. The legs 26 can have various geometries, such as blades or posts, suitable to be secured to the table. In one example, each of the pair of legs 26 are shaped and dimensioned to be inserted to be inserted into accessory clamps C that are customarily associated with fixing accessories attached to an accessory mounting rail R which is coupled to or integral with to operating room tables 40. For example, a lower end 50 of each leg 26 can be shaped and dimensioned with geometry to be inserted into and compatible with the accessory clamps C and accessory mounting rail R. In one embodiment, the lower end 50 of the legs 26 can taper to a relatively narrower width. In addition or alternatively, each leg 26 can have a stop 52 provided at a location along the length of the leg that can abut with either or both of the accessory clamps C or accessory mounting rail R to define a lower limit for the height of the main body 23 above the top surface 42 of the table 40. This can ensure a minimum amount of space for the patient underneath the main body 23 of the support frame 22. The stop 52 could be a projection, an enlarged portion of the leg, a shoulder formed by a tapering of the lower end 50 of the leg, etc.

The support frame 22 can be connected to the pair of legs variously, such as pivotally connected to the pair of legs 26. The two legs 26 may be pivoted from being parallel to the rigid support frame 22 for easy storage to perpendicular with the instrument tray for clinical uses, or to provide quick access to the patient during a medical procedure. In one example, each lateral end of the support frame 22 can be pivotally coupled to one of the legs 26. Each end of the main body 23 can have relatively short depending projections 25 that are rotatably coupled to an upper end 54 of a respective leg 26 by a shaft, bushing, bearing, etc. In another example, the upper end 54 of each leg 26 can be attached to the main body 23 of the support frame 22 and be pivotable relative to the lower end of the leg. In yet another example, an auxiliary support frame with rotatable structure can be arranged between the main support frame and the legs. The pivotable nature of the support frame can be useful to enable the support frame (and receptacle tray, if attached) to be pivoted relatively parallel to the legs, which can provide multiple benefits: (1) pivot the support frame and tray away from the patient's head to provide direct access to the patient; and (2) reduce the storage space required by the protection device (e.g., hung on a wall). It is contemplated that the support frame can freely pivot (e.g., between 0°-90°) or can be keyed to pivot to one or more predetermined angles (e.g., 0°, 30°, 45°, 60°, 90°, etc.). For example, each depending projection 25 can include at least a first hole and a second hole that are positioned so that the upper support surface 24 of the rigid support frame is fixed in one of a first position substantially parallel to said top surface of said operating room table, and a second position arranged substantially 90 degrees to said top surface of said operating room table. Additional holes could be provided on each depending projection 25 to provide additional fixed angles of rotation.

Figure 4:
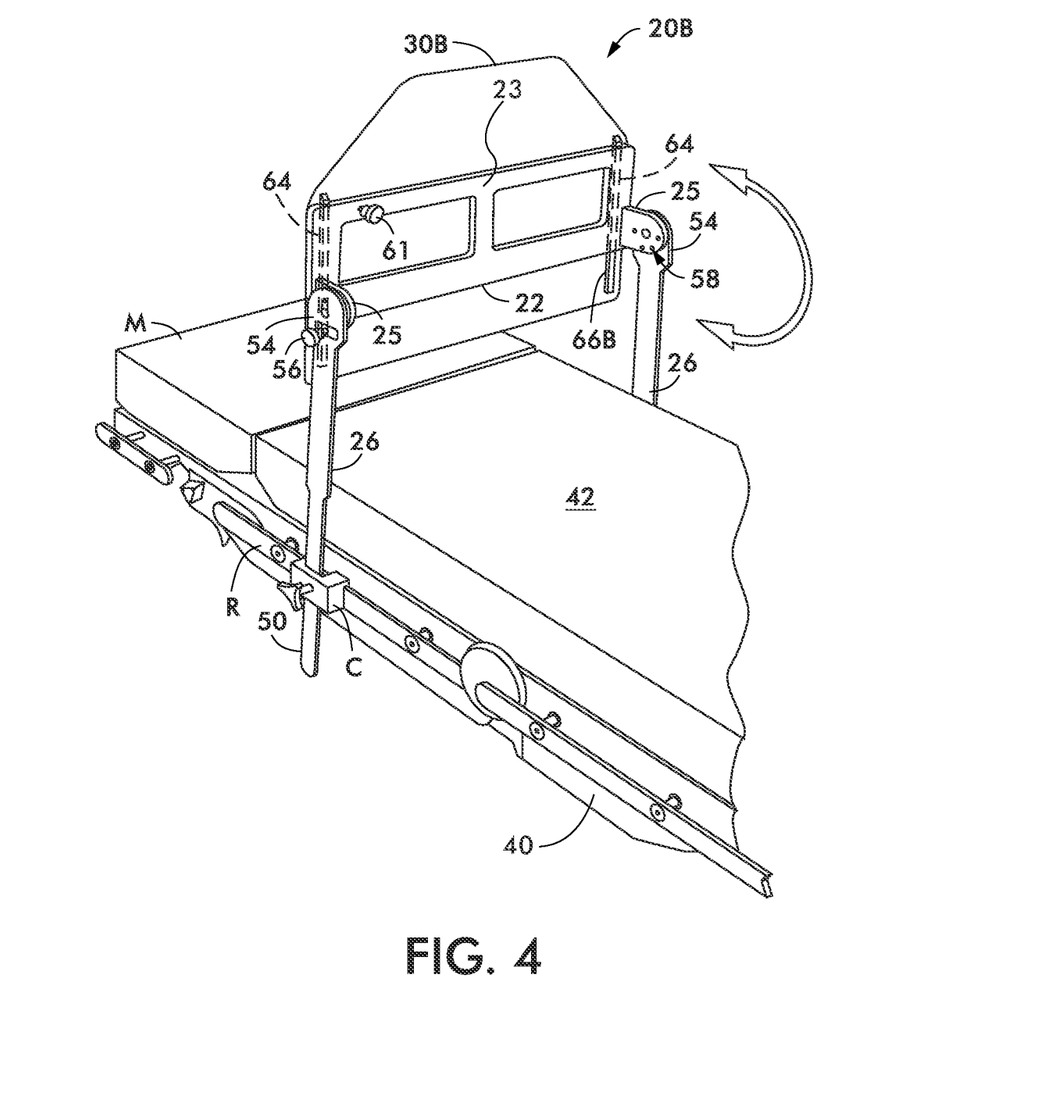
FIG. 4 illustrates the second example patient protection device of FIG. 3 but with the receptacle tray rotated to another position.

Thus, the upper support surface 24 of the rigid support frame can pivot relative to the top surface 42 of the operating room table 40. If intended to be stored on a wall or other vertical surface, any of the support frame, legs, or instrument tray can have suitable wall-hanging structure. The position of each support leg 26 can be held in place by a removable, lockable pin 56 or other fastener that fits into one of two (or more) restraining holes 58 (see FIG. 4) on the depending projections 25 of the main body 23 of the support frame. Preferably, the lockable pin 56 is resiliently biased towards the restraining holes 58, such as by a spring or the like. To rotate the main body 23 of the support frame, the user pulls the spring pin 56 outwards, via a knob, handle, or the like, to disengage the pin 56 from the restraining hole 58. The knob can be manually held open or, in one embodiment, the knob can be turned 90° to lock the pin 56 in an open position that is disengaged from the restraining holes 58. The locked condition of the pin 56 can overcome the spring, if present. The support frame can then be easily rotated to the desired position. During the process of repositioning the support leg, the user could rotate the knob 90° in either direction to release the lock. The unlocked pin 56 will re-seat itself with an audible "click" when it aligns with the new restraining hole 58.

In addition or alternatively, the pair of legs 26 can be secured to the support frame 22 with a fixed width, or could be laterally slidable (i.e., perpendicular to the longitudinal axis L of the table 40) on the support frame 22 to be width-adjustable to be more useful with different tables having different widths and configurations. In one example, the upper end 54 of the legs 26 can be slidably received within a channel or groove formed into the bottom surface of the support frame, or otherwise laterally adjustable on linear slides or even manually movable to different positions, such that the width between the legs 26 is adjusted by sliding or moving either or both legs within their respective channels, lengths, or positions. Preferably, both of the legs 26 are independently width-adjustable, and either can include selective locking structure, such as a locking pin in a hole (preferably a resiliently biased spring pin), clamp, cam-lock, screw-down, detents, etc. The selective locking structure can provide lock down points at specific predetermined widths (i.e., a linear array of holes), or can provide infinite adjustability. The upper end 54 of the leg 26 can be retained within the channel or position in various manners. In one example, the upper end 54 of each leg 26 and the associated channel/position can each have a mating dovetail geometry that permits relative sliding movement while also retaining the end within the channel, although various other geometries are contemplated. In addition or alternatively, any or all of the depending projections 25 could be slidably received within a channel or groove, otherwise laterally adjustable on linear slides or even manually movable to different positions, in a similar manner to provide width adjustability. In one example, the legs 26 can be pivotally coupled to the depending projections 25, as described above, and the width adjustability can be provided by sliding the depending projections 25 upon the main body 23. In addition or alternatively, an end cap can be removably or non-removably secured to the support frame to close off the channel and retain the upper end of the leg. It is also contemplated that the depending projections 25 and/or legs 26 can be width-adjustable using other structure, such as linear slides and the like, clamps with an array of screw-down points, etc. The pair of legs 26 are preferably perpendicular to the upper support surface 24, but can also be arranged a various other angles.

In another embodiment, the support frame 22 can be height adjustable in order to accommodate the patient, accommodate the surgeon, and/or to avoid clashing with robotic arms when the protection device is being employed during robotic assisted surgical interventions. In the shown embodiment, the height of the main body 23 can be adjusted by the selective insertion depth of the lower end 50 of the legs 26 into the accessory clamps C on the accessory mounting rail R. In other examples, the legs 26 and/or depending projections 25 can provide height adjustability, via two or more sliding parts or telescoping structure. In yet another embodiment, the support frame 22 can be of such a fixed height above the operating room table mattress that is standardized, and/or that will avoid clashing with robotic arms when said rigid frame is being employed during robotic assisted surgical interventions. In any event, the protection device provides full access to the patient and full access to medical equipment, such as a breathing apparatus, monitoring sensor(s), IV-administered medications, etc.

Figure 3:
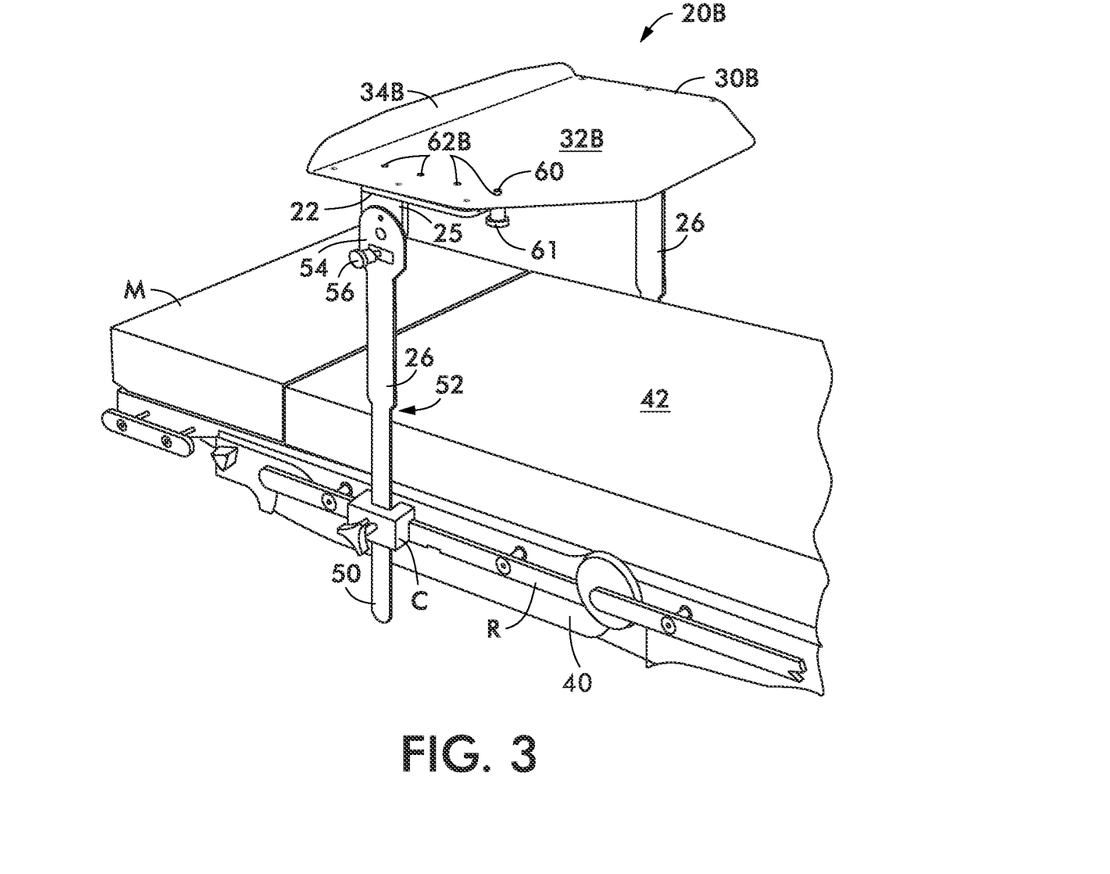
FIG. 3 illustrates a second example patient protection device with a different receptacle tray.

Turning to FIGS. 1 and 3, the second element of the patient protection device, the instrument receptacle tray 30, provides a safe surface for surgeon(s) and assistant(s) to temporarily hold surgical instruments or other medical tools or supplies that are used during any surgical procedure. The receptacle tray 30 provides a stable horizontal surface that is movable relative to the operating table 40 while remaining at a uniform height above the operating table. The receptacle tray 30 is preferably made of durable, rigid materials that are suitable for use in an operating room and surgical setting, such as various metals (e.g., stainless steel, aluminum, etc.) and plastics. Such materials may or may not be radiolucent. Additionally, a sterile material may cover the receptacle tray 30. A removable sterile covering may be used, and the tray can include structure to secure the sterile covering thereto.

Figure 5:
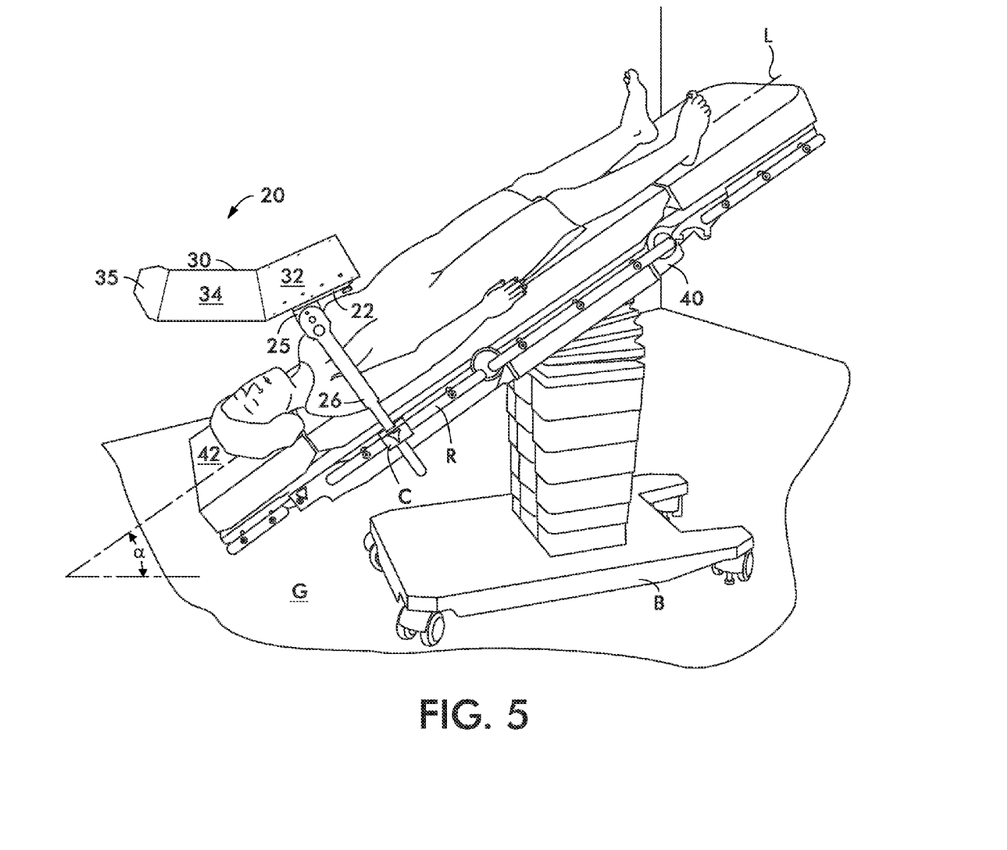
FIG. 5 illustrates the first example patient protection device mounted to a surgery table that is oriented in an angled Trendelenburg position.

Because the patient protection device 20 is intended to be used with surgical tables that can be selectively arranged at different angles (e.g., angled Trendelenburg position) with respect to the ground surface G upon which the table 40 is supported, the receptacle tray 30 may include a single surface or two or more angled surfaces. For example, the receptacle tray 30 can include a first planar surface 32 that is substantially parallel to the top surface 42 of said operating room table 40 (and patient) when the surgical table is at a 0° angle relative to the ground. At this position, the first planar surface 32 is also substantially parallel to the ground surface G that supports the base B of the operating room table 40. The surgical instruments held upon the first planar surface 32 will remain in place and not be dislodged from table. The receptacle tray 30 can also include a second planar surface 34 that is arranged at an angle relative to the first portion, such as a 30°, 45°, or 50° (or other angle) relative to the first portion. Thus, the second planar surface 34 can be substantially parallel or at a slight angle to the ground surface G when the surgical table is pivoted to a similar 30°, 45°, or 50° angle α (or other angle) relative to the ground surface G. Different versions of the receptacle tray 30 can be provided with the second planar surface 34 arranged at different specific angles (e.g., 30°, 45°, or 50° or other angle) each for specific use when the operating room table is positioned at a corresponding angled Trendelenburg angle α. In one example, as shown in FIG. 5, the second planar surface 34 is angled upwards relative to the first planar surface 32 and is located towards the head-end of the table (e.g., the side of the table 40 where the patient's head will be located). Thus, when the head-end of the table 40 is angled downwards, the second planar surface 34 can be substantially parallel or at a slight angle to the ground surface G to provide a relatively flat and stable work surface for the surgical instruments or other medical equipment. Additionally, in the operative position, the first and second planar surfaces are positioned above a body lying over said top surface of said operating room table. Due to the position above the patient's head and face, the receptacle tray 30 can further provide the benefit of protecting the patient's head and face from inadvertent contact by medical personnel or surgical robots. It is contemplated that although identified as planar surfaces, it is understood that these may include partial or completely curved surfaces or minor raised portions, such as where two or more surfaces meet, side edge profiles, raised portions or recesses to retain instruments, etc.

It is further contemplated that the receptacle tray can have three or more portions arranged at different angles, such as a third planar surface 35 or the like. The third planar surface 35 can be intended as another primary surface for surgical instruments for use when the table is at yet another angle, or the third planar surface 35 can be used as an angled stop to inhibit surgical instruments from being accidentally dislodged from the first or second planar surfaces 32, 34. A patient protection device 20B with a second embodiment of the receptacle tray 30B is shown in FIG. 3. For clarity and simplicity, the reference numbers used on the receptacle tray 30B are similar or identical to those items discussed with reference to the receptacle tray 30 of FIG. 1, although are identified with the suffix "B". In this embodiment, the receptacle tray 30B has the first planar surface 32B provided as the primary work surface for the surgical instruments, which is substantially parallel to the top surface 42 of the table 40. A second planar surface 34B is a minor surface used to maintain the surgical instruments upon the primary first planar surface 32B, and in this case is more similar to the third planar surface 35 of the receptacle tray 30 of FIG. 1. The receptacle tray 30B may be useful in situations where the surgical table 40 is maintained at the 0° angle position.

The receptacle tray 30 may be provided as a single monolithic table surface with portions arranged at predetermined angles, although it is further contemplated that one or more surface portions of the receptacle table could be selectively adjustable (e.g., via a hinge or the like) relative to another surface portion to achieve a highly precise angle depending upon the actual tilted angle of the surgical table. Because the predetermined angles of the tray may be somewhat different than the actual tilted angle of the surgical table used by a particular surgeon, any or all of the edges of the receptacle tray can be angled upwards or otherwise include raised stops to retain the surgical instruments. The angled edges can inhibit surgical instruments from rolling off of the tray, and/or inhibit the medical personnel from dislodging them if the tray is accidentally bumped from the side.

Figure 6:
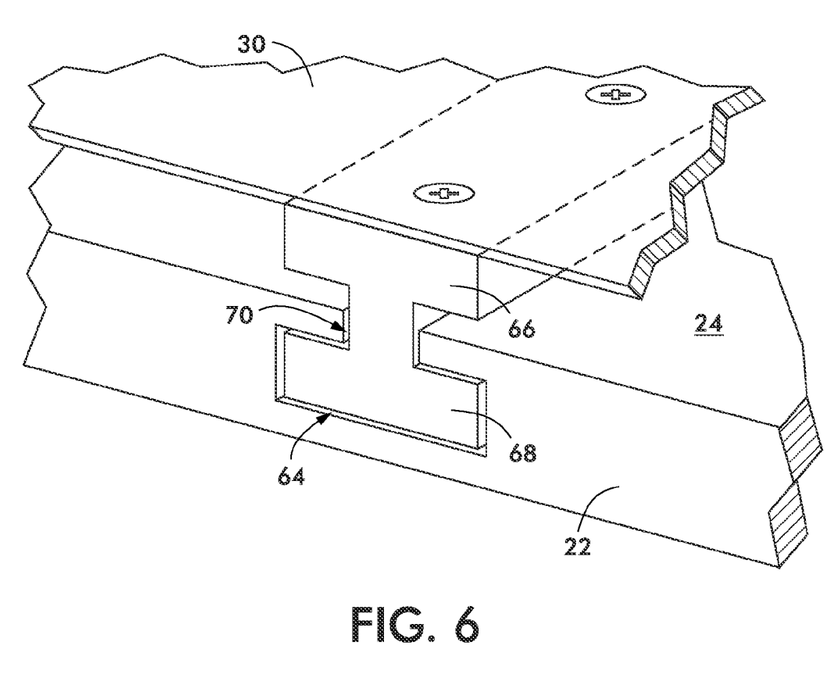
FIG. 6 illustrates a perspective, detail view of a channel of the rigid support frame.

The instrument receptacle tray 30 can be coupled to the support frame 22 in various manners. In one example, the support frame (such as the main body 23 including the upper support surface 24) can define at least one recessed channel 64 that receives at least one corresponding channel insert 66 secured to the bottom of the receptacle tray 30. The channel insert 66 is received within and horizontally slidable along the at least one recessed channel 64 of the rigid support frame 22. Still, it is contemplated that the reverse construction may be used with the tray having the channel, and the support frame having the channel insert. The channel insert can be removably or non-removably secured to the receptacle tray to move therewith. The recessed channel 64 and channel insert 66 can have cooperating geometries. For example, as shown in FIG. 6, the channel insert 66 can have a "T"-shaped or "I-beam"-shaped geometry with an enlarged head 68, while the recessed channel 64 can have a reduced cross-sectional profile 70 that enables the channel insert 66 to slide horizontally therein while resisting or preventing vertical removal of the enlarged head 68 from the channel recess. Preferably, the channel insert 66 is of a relatively softer material as compared to the recessed channel 64, such as a plastic insert received in a metal channel or an aluminum insert in a steel channel, etc., to facilitate sliding therebetween. Still, various different materials can be used for each. Other sliding mechanisms can also be used, such as linear slides, ball-bearing slides, telescoping slides, geared slides, etc. Thus, the position of the receptacle tray can be adjusted with regards to the support frame by sliding the channel insert within the recessed channel. As a result, the receptacle tray 30 is slidable, relative to the rigid support frame 22, along a direction substantially parallel to the upper support surface 24 of the rigid support frame 22.

It is further contemplated that two or more recessed channels 64 and channel inserts 66 can be used, such as one at each lateral edge of the receptacle tray. The use of multiple channels can provide greater stability and/or resistance to lateral or torsional movement of the receptacle tray. In the shown example, two recessed channels 64 are used on either end of the main body 23 of the support frame 22. In another example, three channel and channel insert combinations can be used (e.g., one central and two outboard). Any or all of the multiple channels can utilize fasteners to lock the position of the receptacle tray. For example, in the three-channel version above, only the central channel may include the locking fastener such that there is only one action needed to unlock the tray for fast removal.

In addition or alternatively, the recessed channel 64 of the support frame can be open at either or both ends so that the receptacle tray 30 can be completely removable from the support frame 22 by sliding the tray outwards to a position in which the channel insert 66 is completely removed from the associated recessed channel 64. In one example, the upper support surface 24 of the rigid support frame 22 can include a first edge and an opposed second edge, and the recessed channel 64 can extend substantially across the upper support surface 24 between the first edge and the second edge. As shown in FIG. 2, the recessed channel 64 can extend between the first and second edges along the longitudinal axis L of the table 40 (e.g., in the direction between the head-end and foot-end of the table). Still, it is contemplated that the recessed channel 64 could extend between the first and second edges along a transverse direction of the table 40 (i.e., perpendicular to the longitudinal axis L), or even at other angles. The recessed channels 64 are open at both of the first and second edges of the upper support surface 24 so that the channel insert 66 is slidably removable from the at least one recessed channel at either of the first and second edges.

In an alternative example, the channel insert may be closed at either or both ends, and the channel can include discrete enlarged openings in the upper surface of the support frame in which corresponding independent legs of the channel inserts can be removed when in alignment. Moreover, the fastener used to secure the receptacle tray to the support frame is preferably a quick-action connector, such as a resilient plunger pin, that can be quickly and easily unlocked to permit quick and easy removal of the receptacle tray from the support frame in case of a medical emergency. Once the tray is removed, the medical personnel have greater access to the patient, and especially the patient's head, nose, and mouth, in order to administer necessary life-saving medical care. Additionally, the tray can then be easily replaced, cleaned, or sterilized. Moreover, specially-designed trays can then be easily used with a single support frame.

The receptacle tray 30 can be secured to the support frame 22 in various manners. In one example, the receptacle tray 30 can be coupled to the support frame via one or more fasteners that are received within one or more mounting points or holes of the receptacle tray. For example, the first planar surface 32 of the receptacle tray 30 can include a plurality of holes 62 extending therethrough and the rigid support frame 22 can include a removable pin 60 that is arranged to lockingly engage at least one of the plurality of holes 62 extending through the receptacle tray to thereby inhibit sliding movement of the receptacle tray 30. The reverse construction of parts is also contemplated. The position of the receptacle tray 30 can be linearly adjusted to discrete positions (such as 2, 3, 4, 5 or more positions) with regards to the support frame 22 by selectively positioning the one or more fasteners (e.g., pin 60) in the different holes 62 of the receptacle tray 30. Preferably, the plurality of holes 62 that extend through the receptacle tray 30 are arranged in a linear array that is substantially parallel with the direction of sliding movement of the receptacle tray 30. In another example, the receptacle tray can be slidable with regards to the support frame among several discrete positions (such as 2, 3, 4, 5 or more positions), or can even be infinitely adjustable within a range of positions, such as by use of a threaded fasteners, screw clamps, cam-operated clamps or the like.

Preferably, the fastener used to selectively lock the position of the receptacle tray is located underneath the support frame and receptacle tray so as to not interfere with the surgical instruments. In one example, the removable pin 60 is resiliently biased into locking engagement with at least one of the plurality of holes 62 extending through the receptacle tray 30, such as by a spring pin or the like. This provides the removable pin 60 as resiliently biased in the locked position, such that an affirmative action (i.e., pulling on the pin) is used to unlock the receptacle tray. Thus, to disengage the pin 60 from the hole 62, the user will pull outwards upon a knob 61 or handle. The user can manually hold the knob 61 or handle while adjusting the position of the receptacle tray 30, or pin may even be of a type that, once extended to unlock the tray, can then be rotated to remain in the extended position without further human intervention. For example, the pin 60 can be a twist-lock type in which the knob 61 or handle can be rotated to a locked position that overcomes the spring to maintain the pin 60 in the disengaged position. This can allow the user to complete other tasks without having to hold the knob 61 or handle. After adjusting the position of the receptacle tray 30, the user can then rotate the knob 61 or handle in the opposite direction and permit the spring to re-engage the pin 60 with the desired hole 62. Lastly, the end of the pin 60 may be visible to the user from above the receptacle tray 30 to permit a visual confirmation that the spring pin 60 is in a retaining "stop" or hole 62 prior to draping or otherwise using the receptacle tray 30.

To provide substantially unobstructed access to the patient (and especially the patient's head, nose, and mouth), at least part of the transverse support frame 22 can itself be pivoted out of the way without having to remove the support frame legs 26 from the surgical table 40. This can greatly increase the speed at which the medical personnel can provide emergency care to the patient. The receptacle tray 30 may or may not be removed for this pivoting procedure. In one example, after the receptacle tray 30 is removed, the main body 23 of the support frame 22 can be rotated upwards (e.g., 90° or more relative to the surface of the surgical table) by pulling upon the two knobs (one on each leg 26) outwards to disengage the pin 56 from the restraining hole 58. The main body 23 of the support frame 22 can then be easily rotated upwards to the desired position. The pins can then be re-engaged to lock the main body 23 of the support frame 22 in the rotated position. Then, after patient care is administered, the previous environment can be easily created by reversing the above process. The pins are again pulled outwards, and the main body 23 of the support frame 22 is rotated downwards to be substantially parallel to the top surface 42 of the surgical table 40. The pins are then re-engaged to lock the support frame. If removed, the receptacle tray 30 can then be slidably re-engaged with the channel of the support frame, and locked in the desired position via the lock pin as described above. The receptacle tray 30 can then be re-draped with a sterile covering, and is ready to again support the surgical instruments. Preferably, the pin 56 can be a twist-lock type in which the knob or handle can be rotated to a locked position that overcomes the spring to maintain the pin 56 in the disengaged position, although a manual pin can also be used. If the receptacle tray 30 is still mounted to the support frame 22, then the pivoting movement of the main body 23 of the rigid support frame 22 causes corresponding pivoting movement of the receptacle tray 30. Preferably, the pivoting movement is capable of rotating the receptacle tray 30 to an angle of at least 90 degrees. Additionally, the folded position of the main body 23 can provide easy storage.

In addition or alternatively, the main body 23 of the rigid support frame 22, that defines the upper support surface 24, can include at least one aperture 27 extending through a substantial portion of the upper support surface 24 so that said body lying over said top surface of said operating room table is visible through the at least one aperture 27 when the receptacle tray 30 is removed from the rigid support frame 22. This can be beneficial to allow greater viewing of the patient without having to adjust, pivot, or remove the rigid support frame 22. Two or more apertures 27 may be provided. Preferably, each aperture 27 can extend through 20-60% of the upper support surface 24. Additionally, the use of such apertures 27 can further reduce the weight of the overall system.

The invention creates an environment for patient safety that is capable of holding surgical instruments used during or after any surgical procedure or intervention, while also protecting the head and face of the patient. Additionally, the invention is suitable for use in with the operating table arranged at various angles, such as in the Trendelenburg position. Moreover, the physical profile of the device is not bothersome to surgical assistants.

No other design has attempted to solve these issues in this manner. There are few inventors working on patient protection devices for the operating room and the concept of creating a hybrid utilizing the features of two dissimilar technologies has not been apparent to others. My unique clinical experience, design background, and intimacy in the marketplace are the reason that I am the only person who has created such a device.

The following definitions are provided for terms used herein.

Supine: The patient lays on the table on their back.

Trendelenburg: The table is tilted in the head down position (typically 1 degree to 60 degrees).

Toboggan: Arm restraint that encompasses the arm—named after appearance.

Sled: Arm restraint that holds the restraint pad that encompasses the arm—named after appearance.

Draw Sheet: woven or non-woven sheet placed transversely across the operating room table. Typically used to assist in moving patients. The excess on each side is conventionally used to tuck patient arms.

Neuropathy: An injury to a nerve.

Easily re-closable fasteners: Common reference to hook and loop fasteners (one commercial example is VEL-CRO®).

Anesthesia monitoring lines: Electrically conductive lines attaching certain parts of the body to monitoring systems.

Robot arm: An appendage of the surgical robot (such as the Da Vinci robot) that is capable of holding and operating certain surgical instruments.

AORN: An association of operating room nurses. Considered the governing body with regards to certain guidelines including patient positioning.

IV Infiltration: Typical result of the displacement of the IV needle from the vein into adjoining tissues causing swelling or edema.

Compartment Syndrome: Damage of muscle that is encapsulated in fascia resulting in internal pressures capable of disrupting blood flow to the structure.

Ergonomic arm's length: Anthropomorphic images—showing surgeon stance with arms lowered and 90 degrees to patient.

Surgical Drape: A sterile covering material that typically utilizes a fenestration to isolate the surgical site from the patient. Typical drapes will cover an area approximately 50% larger than the patient.

Lateral: away from the midline.

Medial: toward the midline.

Egg crate foam: Typical a low density foam. Named based on the appearance of the foam configuration.

Surgical table T accessory rail: Most surgical tables have an accessory rail on each side that runs parallel with the table top. They are typically segmented to allow free articulation of table sections.

BMI ratings: A formula utilizing patient size and weight has been utilized to determine.

Body Mass Index: The higher the BMI the more obese the patient.

Perineal cutout: This feature on operating room tables permits optimal access to the patient's perineum.

Perineum: The area located between reproductive structures and the anus.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

What is claimed is:

1. A patient protection device for an operating room table, comprising:
a rigid support frame extending transversely over a top surface of said table, comprising a main body with an upper support surface and a pair of support legs that are secured to said table to inhibit movement of the upper support surface along a longitudinal axis of said table; and
a receptacle tray to receive medical equipment and being securely mounted to the rigid support frame via a removable connection, the receptacle tray comprising a first planar surface that is substantially parallel to said top surface of said operating room table and a second planar surface arranged at an angle relative to the first planar surface,
wherein the receptacle tray is slidable, relative to the rigid support frame, along a direction substantially parallel to the upper support surface of the rigid support frame,
wherein, in an operative position, the first and second planar surfaces are positioned above a body lying over said top surface of said operating room table, and
wherein the first planar surface of the receptacle tray comprises a plurality of holes extending therethrough and the rigid support frame comprises a removable pin that is arranged to lockingly engage at least one of the plurality of holes extending through the receptacle tray to thereby inhibit sliding movement of the receptacle tray.

2. The patient protection device of claim 1, wherein each support leg of the rigid support frame comprises an upper end that is secured to the main body of the rigid support frame, and a lower end that is shaped and dimensioned to be inserted into accessory clamps associated with an accessory mounting rail upon said operating room table.

3. The patient protection device of claim 2, wherein the main body of the rigid support frame comprises a pair of depending projections that are each secured to the upper end of a selected one of the support legs of the rigid support frame.

4. The patient protection device of claim 3, wherein each support leg is secured to said selected one of the depending projections by a removable pin.

5. The patient protection device of claim 4, wherein each support leg is pivotally connected to said selected one of the depending projections so that the main body and upper support surface of the rigid support frame can pivot relative to said top surface of said operating room table.

6. The patient protection device of claim 5, wherein pivoting movement of the main body of the rigid support frame causes corresponding pivoting movement of the receptacle tray, and wherein the pivoting movement is capable of rotating the receptacle tray to an angle of at least 90 degrees.

7. The patient protection device of claim 1, wherein a main body of the rigid support frame, that defines the upper support surface, comprises at least one aperture extending through a substantial portion of the upper support surface so that said body lying over said top surface of said operating room table is visible through the at least one aperture when the receptacle tray is removed from the rigid support frame.

8. The patient protection device of claim 1, wherein the removable pin is resiliently biased into locking engagement with at least one of the plurality of holes extending through the receptacle tray.

9. The patient protection device of claim 1, wherein the plurality of holes extending through the receptacle tray are arranged in a linear array that is substantially parallel with the direction of sliding movement of the receptacle tray.

10. The patient protection device of claim 1, wherein the pair of support legs are laterally slidable with respect to the main body along a direction that is perpendicular to the longitudinal axis of said table to thereby selectively adjust a width between the pair of support legs.

11. A patient protection device for an operating room table, comprising:
  a rigid support frame extending transversely over a top surface of said table, comprising a main body with an upper support surface and a pair of support legs that are secured to said table to inhibit movement of the upper support surface along a longitudinal axis of said table; and
  a receptacle tray to receive medical equipment and being securely mounted to the rigid support frame via a removable connection, the receptacle tray comprising a first planar surface that is substantially parallel to said top surface of said operating room table and a second planar surface arranged at an angle relative to the first planar surface,
  wherein the receptacle tray is slidable, relative to the rigid support frame, along a direction substantially parallel to the upper support surface of the rigid support frame, and wherein, in an operative position, the first and second planar surfaces are positioned above a body lying over said top surface of said operating room table,
  wherein the rigid support frame comprises at least one recessed channel and the receptacle tray comprise at least one channel insert that is received within and horizontally slidable along the at least one channel of the rigid support frame.

12. The patient protection device of claim 11, wherein the upper support surface of the rigid support frame comprises a first edge and an opposed second edge, and the at least one recessed channel extends substantially across the upper support surface between the first edge and the second edge, and
  wherein the at least one recessed channel is open at both of the first and second edges of the upper support surface so that the channel insert is removable from the at least one recessed channel at either of the first and second edges.

13. A patient protection device for an operating room table, comprising:
  a rigid support frame extending transversely over a top surface of said table, comprising a main body with an upper support surface and a pair of support legs that are secured to said table to inhibit movement of the upper support surface along a longitudinal axis of said table; and
  a receptacle tray to receive medical equipment and being securely mounted to the rigid support frame via a removable connection, the receptacle tray comprising a first planar surface that is substantially parallel to said top surface of said operating room table and a second planar surface arranged at an angle relative to the first planar surface,
  wherein the receptacle tray is slidable, relative to the rigid support frame, along a direction substantially parallel to the upper support surface of the rigid support frame, and wherein, in an operative position, the first and second planar surfaces are positioned above a body lying over said top surface of said operating room table,
  wherein the receptacle tray further comprises a third planar surface arranged at an angle relative to both of the first and second planar surfaces.

14. A patient protection device for an operating room table, comprising:
  a rigid support frame extending transversely over a top surface of said table, comprising a main body defining an upper support surface with a recessed channel, a pair of depending projections extending downwards from the main body, and a pair of support legs each connected to a selected one of the depending projections and secured to said table to inhibit movement of the upper support surface along a longitudinal axis of said table,
  wherein each support leg is pivotally connected to said selected one of the depending projections of the main body of the rigid support frame so that the main body of the rigid support frame can pivot relative to said top surface of said operating room table; and
  a receptacle tray to receive medical equipment and being securely mounted to the rigid support frame via a removable connection, the receptacle tray comprising a first planar surface that is substantially parallel to said top surface of said operating room table, and a channel insert that is received within and horizontally slidable along the recessed channel of the rigid support frame so that the receptacle tray is slidable, relative to the rigid support frame, along said longitudinal axis of said table,
  wherein, in an operative position, the first planar surface is positioned above a body lying over said top surface of said operating room table.

15. The patient protection device of claim 14, wherein the first planar surface of the receptacle tray comprises a plurality of holes extending therethrough that are arranged in a linear array extending along a direction of the longitudinal axis of said table, and
  wherein the rigid support frame comprises a removable pin that is resiliently biased into locking engagement with at least one of the plurality of holes extending through the receptacle tray to thereby inhibit slidable movement of the receptacle tray.

16. The patient protection device of claim 14, wherein the channel insert comprises a "T"-shaped or "I-beam"-shaped geometry with an enlarged head, and the recessed channel comprises a corresponding reduced cross-sectional profile that enables the enlarged head to be horizontally slidable along the channel recess while preventing the enlarged head from being vertically removable from the channel recess.

17. The patient protection device of claim 14, wherein each support leg is secured to said selected one of the depending projections of the main body of the rigid support frame by a removable pin that is received within one of a first and second hole on said selected one of the depending projections, and
  wherein the first and second holes are positioned so that the upper support surface of the rigid support frame is fixed in one of a first position substantially parallel to said top surface of said operating room table and a second position arranged substantially 90 degrees to said top surface of said operating room table.

18. The patient protection device of claim 14, wherein the recessed channel extends substantially across a width of the upper support surface of the rigid support frame between a first edge and a second edge thereof that are each open so that the channel insert is removable from the recessed channel at either of the first and second edges and the receptacle tray is thereby completely removable from the rigid support frame.

19. The patient protection device of claim 14, wherein the receptacle tray further comprises a second planar surface arranged at an angle relative to the first planar surface,
wherein the angle of the second planar surface is oriented to be substantially parallel to a ground surface that said operating room table is supported on when said top surface of said operating room table is positioned in an angled Trendelenburg position.

20. The patient protection device of claim 14, wherein the pair of support legs are laterally slidable with respect to the main body along a direction that is perpendicular to the longitudinal axis of said table to thereby selectively adjust a width between the pair of support legs.

* * * * *